United States Patent
Vesel et al.

(10) Patent No.: US 6,525,323 B1
(45) Date of Patent: Feb. 25, 2003

(54) METHOD AND APPARATUS FOR IMPROVED ESTIMATION OF CHARACTERISTICS OF PULSES DETECTED BY A NUCLEAR CAMERA

(75) Inventors: John F. Vesel, Kirtland, OH (US); Micheal J. Petrillo, Pleasanton, CA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/551,092

(22) Filed: Apr. 18, 2000

(51) Int. Cl.[7] .............................. G01T 1/20; G01T 1/02
(52) U.S. Cl. .................................. 250/369; 250/363.07
(58) Field of Search ........................... 250/369, 363.07, 250/363.09

(56) References Cited

U.S. PATENT DOCUMENTS 5,270,547 A * 12/1993 Stark et al. .................. 250/369
5,508,524 A *  4/1996 Goldberg et al. ............ 250/369
6,291,825 B1 *  9/2001 Scharf et al. ................ 250/369

OTHER PUBLICATIONS

Variable Sampling–Time Technique for Improving Count Rate Performance of Scintillation Detectors, By Eiichi Tanaka, Norimasa Nohara, and Hideo Murayama; Jun. 2, 1998.

Evaluation of a Clinical Scintillation Camera with Pulse Tail Extrapolation Electronics, By Thomas K. Lewellen, Alden N. Bice, Kenneth R. Pollard, Jai–Bi Zhu, and Marianne E. Plunkett; Apr. 25, 1989.

* cited by examiner

*Primary Examiner*—Georgia Epps
*Assistant Examiner*—Alicia M Harrington
(74) *Attorney, Agent, or Firm*—Fay, Sharpe, Fagan, Minnich & McKee, LLP (57) ABSTRACT

A nuclear medicine imaging device includes a radiation camera (10) including a plurality of photo multiplier tubes (28). Each photo multiplier tube (28) is configured with an analog to digital converter (30) which converts a detected scintillation event (50) to sampled digital values. A storage device (66) is preloaded with an estimator function which can be derived from a calibration scintillation events. A processor (14) in communication with both the camera (10) and the storage device (66), detects an event and combines the digital values which are sampled together to arrive at a total area or energy of the scintillation event. Alternately, if a second pulse (52) is detected before the first scintillation event (50) has ended, the area combining ($A_1$) of the first event is stopped and a pulse tail is estimated ($A_2$) from the estimator functions stored. This estimated tail is then added to the combined data values taken until the time of pile-up. Additionally, the estimated tail ($A_2$) is subtracted from the combined data values for the second scintillation event (52).

20 Claims, 7 Drawing Sheets

| TIME  | 1    | 2   | 3   | 4    | 5    | 6    | 7   | 8    | 9   | 10   | 11   | ... | T-2  | T-1  | T |
|-------|------|-----|-----|------|------|------|-----|------|-----|------|------|-----|------|------|---|
| RATIO | 0.01 | 0.1 | 0.2 | 0.32 | 0.39 | 0.41 | 0.5 | 0.55 | 0.6 | 0.65 | 0.67 | ... | 0.98 | 0.99 | 1 |

METHOD AND APPARATUS FOR IMPROVED ESTIMATION OF CHARACTERISTICS OF PULSES DETECTED BY A NUCLEAR CAMERA

BACKGROUND OF THE INVENTION

The present invention relates to the art of nuclear medicine and diagnostic imaging. It finds particular application in conjunction with positron emission tomography (PET), and will be described with particular reference thereto. It is to be appreciated that the present invention is amenable to single photon emission computed tomography (SPECT), whole body nuclear scans, positron emission tomography (PET), Compton scattering, other diagnostic modes and/or other like applications. Those skilled in the art will also appreciate applicability of the present invention to other applications where a plurality of pulses tend to overlap, or "pile-up" and obscure each other.

Diagnostic nuclear imaging is used to study a radio nuclide distribution in a subject. Typically, one or more radiopharmaceutical or radioisotopes are injected into a subject. The radiopharmaceutical are commonly injected into the subject's bloodstream for imaging the circulatory system or for imaging specific organs which absorb the injected radiopharmaceutical. A gamma or scintillation camera detector head is placed adjacent to a surface of the subject to monitor and record emitted radiation. Often, the detector head is rotated or indexed around the subject to monitor the emitted radiation from a plurality of directions. This data is reconstructed into a three-dimensional image representative of the radiopharmaceutical distribution within the subject.

Each detector head typically includes an array of photo multiplier tubes facing a large scintillation crystal. Each received radiation event generates a corresponding flash of light that is seen by the closest photo multiplier tubes. Each photo multiplier tube that sees an event puts out a corresponding analog pulse, pulses from tubes closest to the flash being bigger than pulses from further away tubes. The analog pulses from the individual PMT's are digitized and combined digitally to generate x and y spatial coordinates approximating the location of the scintillation event in the crystal.

As demands are made for increased patient throughput and improved image quality, the detector heads are subjected to increasing volumes of gamma ray events per second. For example, in a PET scanner in order to obtain about 150 coincident events per second, each detector head typically receives on the order of 2,000,000 events per second. Indeed, one way to increase scanning speed is to increase the number of events per second. Undesirably, as the number of events per second increase, scintillation pulse events begin to overlap to a greater and greater extent leading to pulse loss and other image degradations.

To accommodate higher count rates, current emission detector heads shorten the pulse tails produced by some of the photo multiplier tubes, reducing perceived event overlap. This analog technique is known as delay line clipping. This method desirably reduces the effect of pulse pile-up. However it tends to degrade spatial and energy resolution of a gamma camera if a commensurate shortening of integration time occurs. Moreover, scintillation pulses or events that occur without a pile-up are also subject to delay line clipping. In other words, even when the problem of pulse pile-up is not present, the signals are still clipped. This is typically seen as an engineering compromise between count rate and energy and spatial resolution. An additional technique to reduce the effects of pile-up employs the use of an analog signal extrapolation circuits to correct both the initial or first pulse, and a following pulse. Unfortunately, the number of pulses that can be corrected is limited by the number of estimator/amplifier circuits.

The present invention contemplates a new and improved method and apparatus which overcomes the above-referenced problems and others.

SUMMARY OF THE INVENTION

In accordance with one embodiment of the present invention, a nuclear camera includes detector heads mounted for movement around an examination region and a processor for reconstructing signals from the detector heads into an image representation. Each detector head includes a scintillation crystal that converts each received radiation event into a flash of light. The detector heads also include an array of photo multiplier tubes arranged to receive the light flashes and, in response, generate an analog tube output pulse. A plurality of analog-to-digital converters convert the analog tube output pulse for each photo multiplier tube to a series of digital tube output values. A processor reconstructs the image representation from the digital tube output values.

In accordance with another aspect of the present invention, a nuclear camera further includes a storage device loaded with an estimator function derived from a calibration radiation event. The processor integrates the series of digital values corresponding to each pulse until the end of the pulse or the beginning of another overlapping pulse is detected. In response to detection of the overlapping pulse, the processor accesses the estimator function in the storage device to estimate a remainder of the first pulse.

In accordance with another aspect of the present invention, the estimator function includes a plurality of ratios of portions of the calibration event at selected sampling times. The processor includes a multiplier for multiplying a ratio corresponding to a sampling characteristic of the first event at the time which the second event is detected and the integrated digital values between detection of the first and the second events. This produces an estimated remainder. An adder is also provided for adding the integrated digital values and the estimated remainder together to arrive at an estimate of the first event.

In accordance with another aspect of the present invention, the estimator function includes a plurality of estimated remainders corresponding to integrated digital values and sampling times. The processor adds the integrated digital values and the corresponding estimated remainder to provide an estimate of the first scintillation event.

In accordance with another embodiment of the present invention, in a medical imaging device for imaging an area of interest by detecting radiation events, a method of estimating truncated events includes determining at least one estimator function for the medical imaging device by sampling one calibration event at least. The method further includes detecting a first event of interest followed by detection of a second event interrupting the first event of interest. Based on the estimator function, a remainder of the first event of interest is estimated following detection of the interrupting second event.

In accordance with another aspect of the present invention, the method further includes digitally sampling the detected first event at a predetermined sampling rate while combining the digital samples. Upon detection of the second event, the combining of samples is ceased.

In accordance with another aspect of the present invention, the method further includes totaling the combined digital samples of the detected event and the estimated remainder resulting in an estimate of the entire first event.

In accordance with another aspect of the present invention, the determining an estimator function includes calculating ratios of combined digital samples at selected sampling times, to a sum of digital samples combined over the entire calibration event.

In accordance with another aspect of the present invention, the estimating a remainder step includes based on a sampling time substantially coincident with the detection of the interruption, retrieving a calculated ratio. The combined digital sample is then multiplied with the retrieved ratio resulting in an estimate of the remainder of the first event.

In accordance with another aspect of the present invention, the determining an estimator function includes associating combined digital samples from the calibration event with the calculated ratios to produce a plurality of remaining area estimates.

In accordance with another aspect of the present invention, the estimating a remainder step includes determining a one of the remaining area estimates corresponding to combined digital samples and a sample time of detection of the second event.

In accordance with another aspect of the present invention, upon detection of the second event, samples of the coincident events are combined, and the estimated remainder of the first event is removed from the combination to yield an estimate of the second event.

In accordance with another embodiment of the present invention, a method of estimating an energy of an event detected by a medical imaging device includes detecting a first event. The detected event is sampled at a defined sampling rate while samples from the detected event are combined. When a second event is detected, partially coincident with the first event, the combining is ceased. A remainder representing an estimate of combined samples of the first event is estimated following detection of the second event.

In accordance with another aspect of the present invention, the method further includes for the first event, totaling the combined samples of the detected first event and the estimated remainder of the first event thus producing an estimate of the first event.

In accordance with another aspect of the present invention, the method further includes on detection of the second event, combining sampled values to generate a second event combined value. The estimated remainder of the first event is removed from the second combined value, yielding an estimate of the second event.

In accordance with another aspect of the present invention, the method further includes determining a family of estimator functions for the medical imaging device from calibration events.

In accordance with another aspect of the present invention, the estimator function determining step includes calculating ratios of combined samples up to selected sampling times, to combined samples over the entire calibration event.

In accordance with another aspect of the present invention, the remainder estimating step includes, based on a sampling time substantially coincident with the detection of the second event, retrieving a corresponding ratio. The combined samples of the first event are then multiplied with the retrieved ratio, yielding an estimate of the remainder.

In accordance with another aspect of the present invention, the estimator function determining step further includes combining calibration samples up to selected times with the corresponding ratios thereby producing a plurality of remaining area estimates.

In accordance with another aspect of the present invention, the remainder estimating step includes retrieving a remaining area estimate based on combined samples of the first event before detection of the second event, and the detection time of the second event.

In accordance with another aspect of the present invention, the remainder estimating step includes determining an area under at least two points of an estimated pulse tail curve generated from the calibration events.

One advantage of the present invention resides in improved energy and spatial resolution.

Another advantage is that pulse tail estimation is not limited to fixed integration times. The pulse can be integrated to the maximum integration time when pulse pile-up does not occur.

Another advantage of the present invention resides in the elimination of extra extrapolation/amplifier circuits. The correction for pulse pile-up can be completed at the sampling rate of the digital sampling circuitry without extra circuits to handle multiple pile-up events.

Yet another advantage of the present invention resides in a calibration procedure using a statistically significant number of pulses to determine the estimator function. The estimator only assumes that the pulse shape is consistent for the correction to be accurate. In other words, no knowledge of the pulse shape is required. Different estimator coefficients can be selected for a given channel's optics or electronics or operating environment, such as temperature.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not be construed as limiting the invention.

DETAILED DESCRIPTION OF THE PREFERRED EMBODIMENTS

Figure 1:
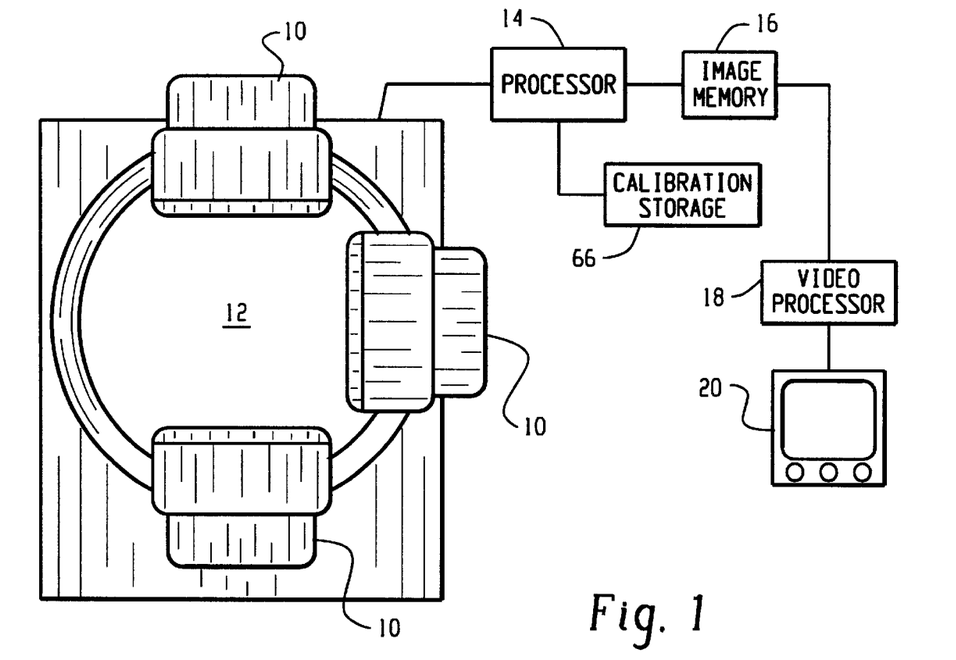
FIG. 1 is a diagrammatic illustration of a nuclear medicine imaging device in accordance with the present invention.

With reference to FIG. 1, a nuclear medicine imaging machine includes a number of imaging cameras 10 circumferentially about a region of interest 12. Typically, an object from which images are desired is injected with one or more radiopharmaceutical or radioisotopes and placed in the region of interest 12. The presence of these pharmaceuticals within the object produces emission radiation from the object, a certain amount of which is detected by the cameras 10. The cameras are positionable radially and circumferentially to optimize data acquisition. The heads are angularly indexed or rotated to collect emission data from a plurality of directions. A processor 14 receives the event and head orientation data from the cameras 10 and processes the information into a volumetric image representation defined by radiation received by each camera at each coordinate. The image representation is then stored in an image memory 16 for manipulation by a video processor 18 and display on an imaging display 20.

Figure 2:
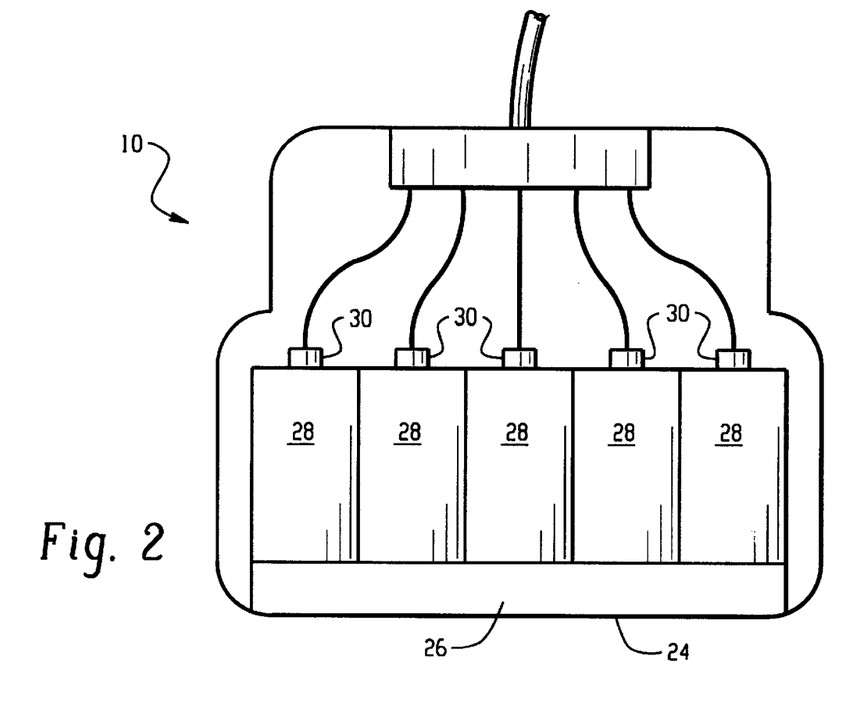
FIG. 2 is an enlarged view of one of the cameras of FIG. 1, cut away to partially reveal internal elements.

Referring now to FIG. 2, each camera has a radiation receiving face 24 facing the area of interest 12. The receiving face 24 typically includes a scintillation crystal, such as a large doped sodium iodide crystal 26, that emits a flash or scintillation of light or photons in response to incident radiation. An array of photo multiplier tubes 28 receive the light and convert it into electrical signals. An analog to digital converter 30 is associated with the output of each photo multiplier tube 28 for converting its analog, electrical output signal into a series of digital values. The digital outputs of the converters 30 following each scintillation event are processed and corrected to generate an output signal indicative of (1) a position coordinate on the detector head at which each radiation event is received, and (2) an energy value of each event. The energy is used to differentiate between various types of radiation and to eliminate noise and scattered radiation.

Figure 3:
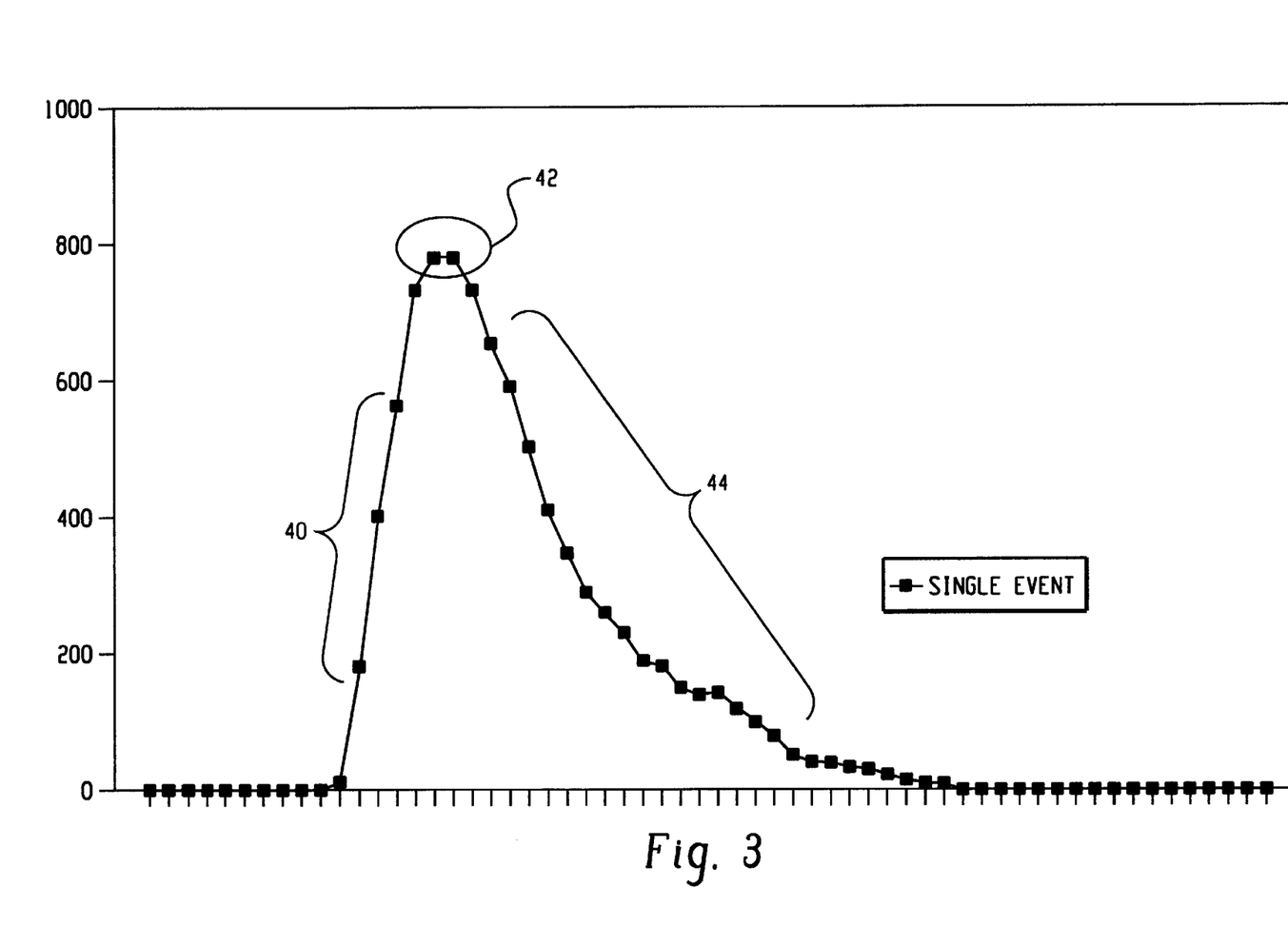
FIG. 3 is a graphical depiction of a digitized pulse from the analog to digital converter.

Referring now to FIG. 3, a graphical depiction of a digitally sampled scintillation event typically includes a rapidly changing portion 40, which reaches a peak 42 and a gradual decreasing tail portion 44. For the processor to determine the energy of the event, the area underneath the curve is determined. The signal is digitally sampled at a rate sufficient to capture an appropriate number of amplitude values. A rate between 40 to 70 MHZ was found to provide a useful number of samples. Artisans appreciate with further reference to FIG. 3, that the integration or combination of sample data points is relatively straight forward in the event of a single scintillation event. The combining becomes problematic when several pulses overlap, a condition known as pile-up.

Figure 4:
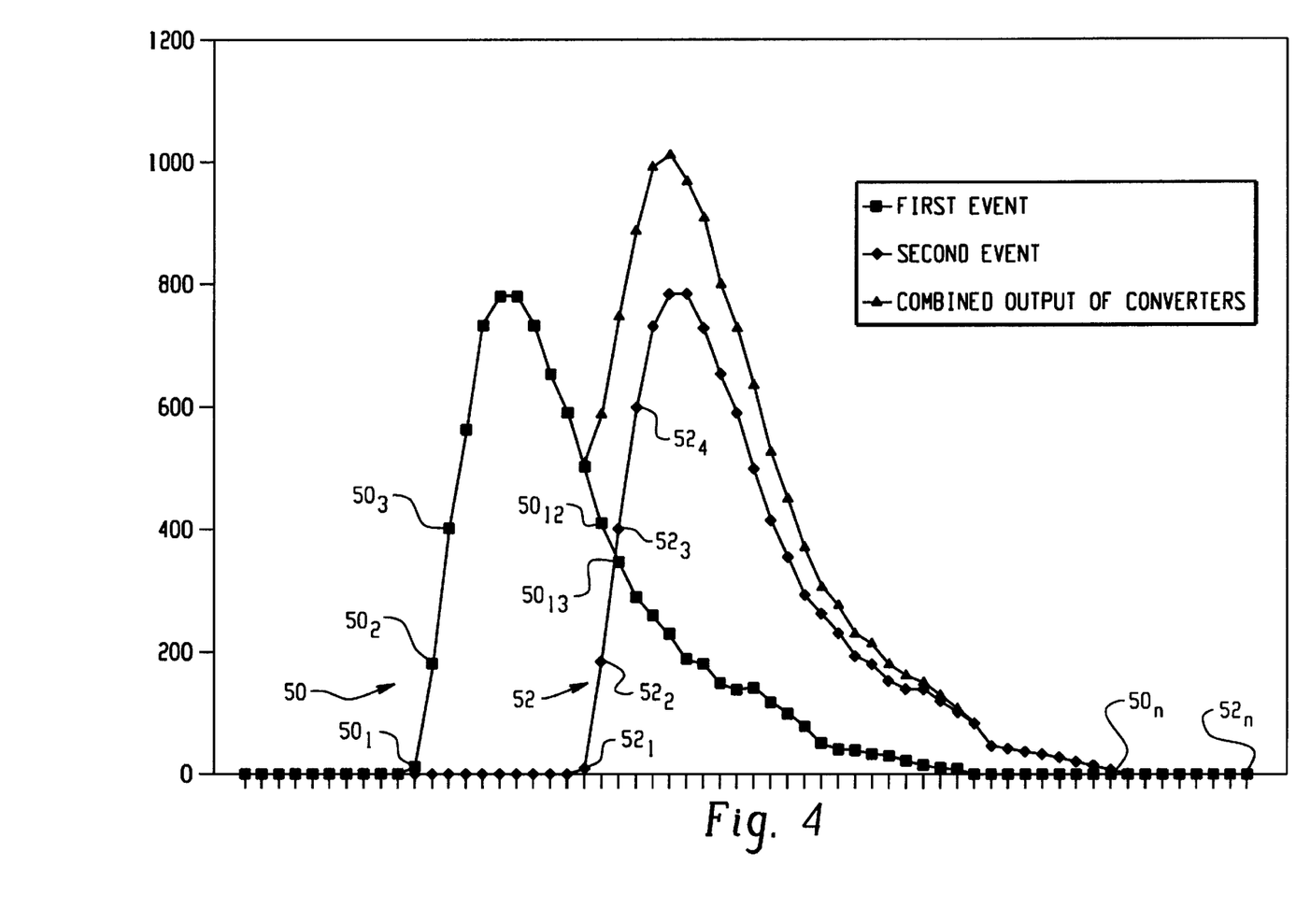
FIG. 4 is a graphical depiction of a pulse pile-up event.

Referring now to FIG. 4, a graphical depiction of pulse pile-up situation is illustrated. As an example, a first event 50 is detected during an imaging procedure. As the digital values $50_1$, $50_2$, $5_3$, . . . $50_n$ are forwarded to the processor for combination, the processor is also searching for a second scintillation event. Upon detection of a near concurrent second event 52, at substantially the same location, the output of the analog to digital converters 30 combine the signal attributable to the second event to the signal attributable to the first event. The processor 14 resolves the two pulses, e.g. by analyzing slope changes, and estimates the missing rail $50_{12}$–$50_n$ of the first pulse. To determine the value for the remainder of the pulse tail of the first event, the processor retrieves an estimation function (more fully discussed below), and applies this function to derive an estimate of the complete pulse area of the first event. Those skilled in the art will appreciate that once an estimate is obtained of the remainder of the first event 50, the remainder can be subtracted from the combined values of the second scintillation event 52 to also yield an effective estimate of that pulse. Accordingly, the ability to estimate accurately the pulse tail upon a pile-up event produces more accurate overall pulse values improving both energy and spatial resolution at any given count rate.

Figure 5:
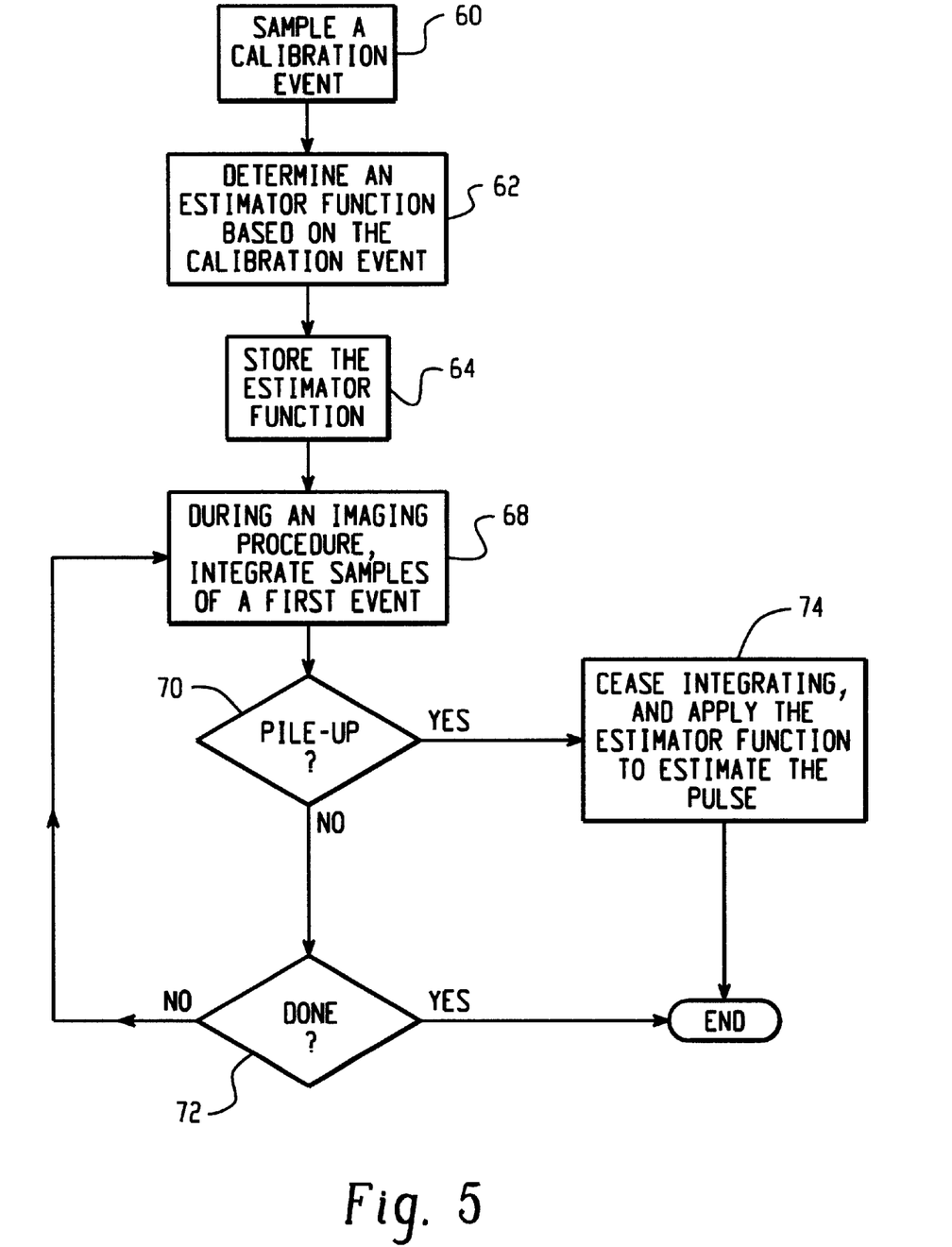
FIG. 5 is an exemplary flowchart which suitably embodies the present invention.

With reference now to FIG. 5, an exemplary flow chart is provided illustrative of the tasks a processor 14 accomplishes. Initially, a clean, single calibration event is sampled 60. An estimator function is then determined 62 based on the calibration event. The estimator function is stored 64, for example, in a calibration function storage device 66 (FIG. 1). During a subsequent imaging procedure, a first event is detected, and the outputs of the analog-to-digital converters 30 (FIG. 2) are sampled 68 at a specified sampling rate. While individual samples are being combined, the system continues to be monitor 70 for a pile-up condition, i.e. a second scintillation event, occurring before the end of the tail of the preceding event. Additionally, the system continues to monitor status of the combination for the first event, as indicated by decision block 72. In other words, as long as only the first event is detected, its values are sampled and integrated until the end of the event or a pile-up event occurs. Comparison with the calibration event, slope, time amplitude, and the like can be used to determine the end of a pulse.

In the event no pile-up event occurs, the first event is sampled until it is completed. In the case of only a single event occurring, the area or energy of the scintillation event is determined merely by adding or integrating each of the individual samples. On the other hand, if a pile-up event is detected by the decision block 70, the integrating is stopped and the estimator function is applied to estimate the area under the cut-off tail. This estimate is combined 74 with the previously integrated sample values, yielding an estimate of the area or energy of the first event.

Figure 6A:
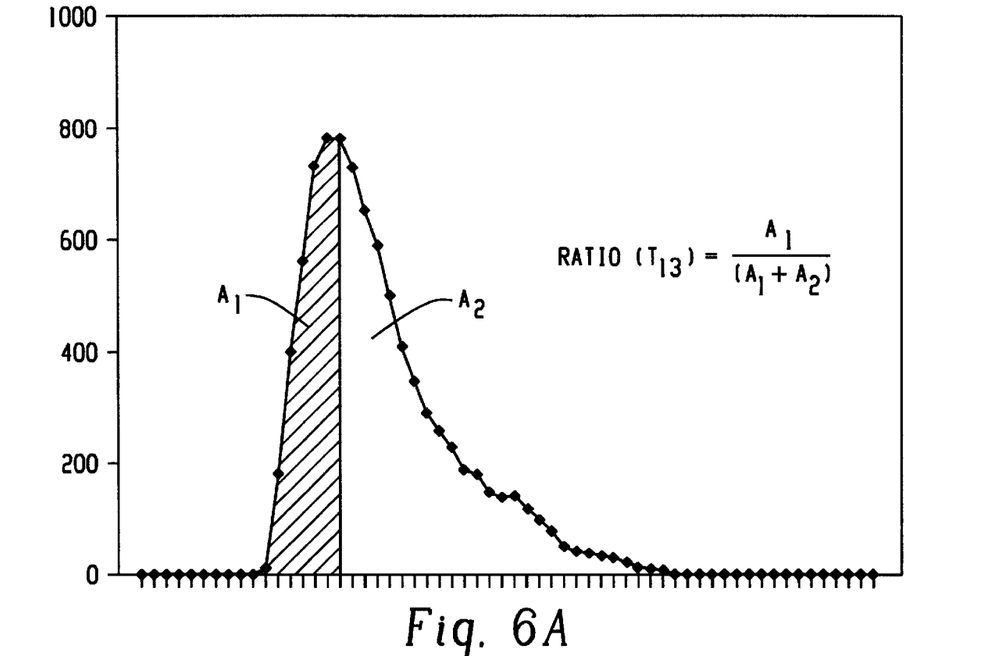
FIGS. 6A, B, and C are embodiments according to the present invention of estimating the tail portion of an event in response to detection of a pile-up.
Figure 6B:
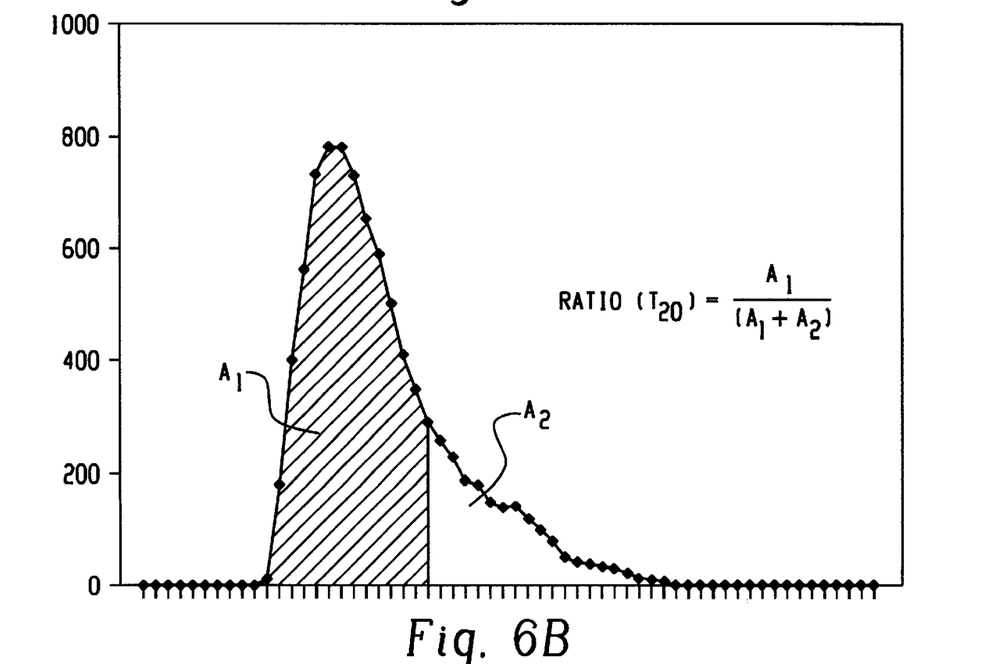
Figure 6C:
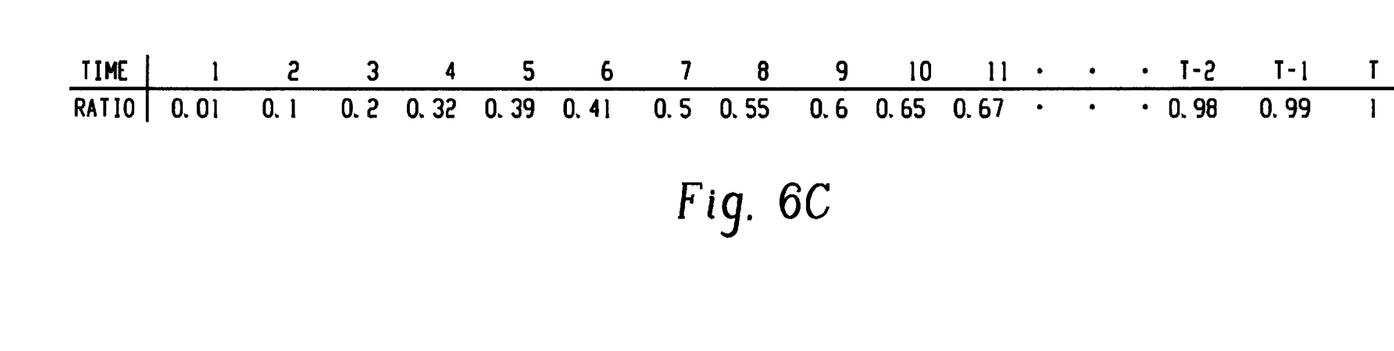

Several alternatives are available to derive the estimator function. Referring now to FIGS. 6A, B, and C, a calibration event is detected and sampled over some period determined to be representative of an entire scintillation event, for example a thirty clock cycle event. For each sample time, ratios are calculated of the area measured at that sample time to the total area of the entire event. Those skilled in the art will appreciate that for the calibration events, sub-total areas are stored for each sample time. Later, at the end of the calibration period, ratios of area at each time to the total area are determined. For example with reference to FIG. 6A, the ratio at time $T_{13}$ represents a small portion of the total area under the curve. Differently, the ratio depicted in FIG. 6B represents a larger portion of the total area.

Once ratios have been determined for each sample, these ratios are stored in calibration storage 66 (FIG. 1), for example in a format depicted by FIG. 6C. During operation, when a pile-up of events is detected, the ratio/estimator function corresponding to the beginning of the second event is retrieved from storage 66. The inverse of the retrieved ratio is multiplied with the area calculated at the time of the pile-up (i.e. $A_1$) resulting in an estimate of the remaining area for the pulse (e.g. $A_2$). At this point an estimate of the entire pulse is determined by adding $A_1$ and $A_2$. In other words, the processor performs one multiplication and one addition. Those skilled in the art will appreciate that these ratios may be refined by adjusting them for different operating conditions, such as crystal temperature, or signal processing channel, since variations may exist depending on such properties of the system.

Figure 7:
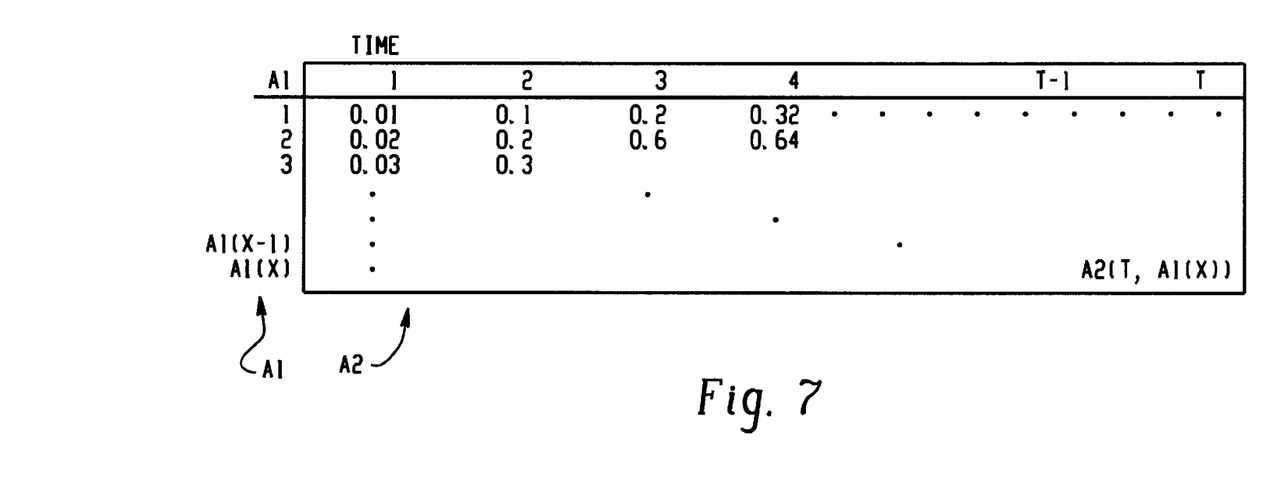
FIG. 7 is an embodiment of the architecture of the storage device suitable to practice the present invention.

With reference now to FIG. 7, the calibration storage 66 (FIG. 1), alternately is configured to include estimated tail areas (i.e. $A_2$) based on inputs of combined sample area ($A_1$), time, and other variables. This arrangement collects more calibration data for storage with the benefit of reducing the number of mathematical operations required of the processor, hence increasing speed. In other words, the processor will query the calibration storage 66 and retrieves an area estimate $A_2$ instead of a ratio. Thus, the processor 26 need only combine the returned estimated value $A_2$ with the combined sample value $A_1$ at pile-up time to estimate the scintillation pulse.

Figure 8:
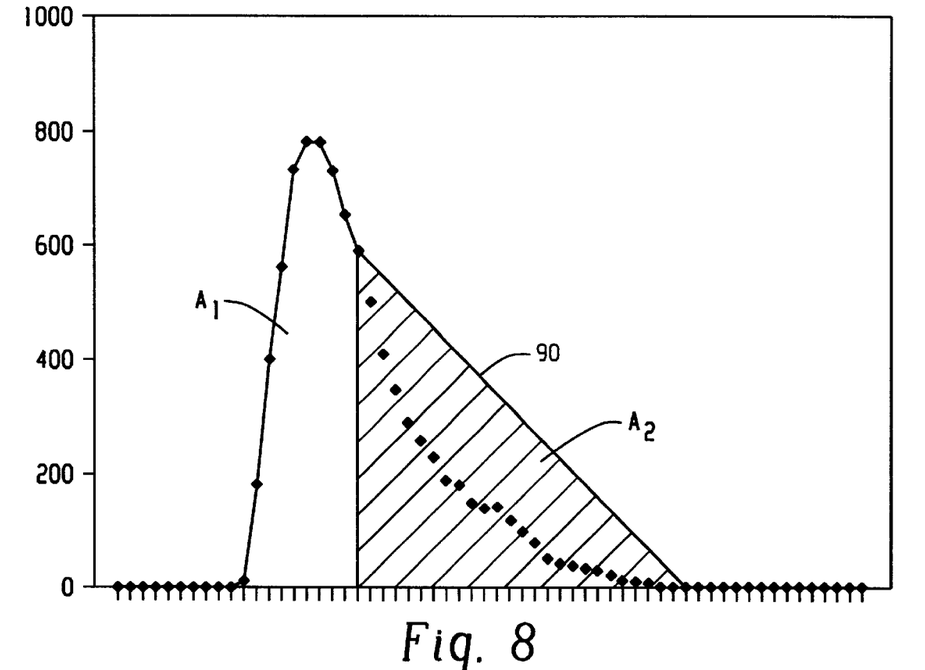
FIG. 8 is an illustration of an alternate pulse tail remainder estimator function; and, FIG. 9 is another alternate pulse tail remainder estimator function.
Figure 9:
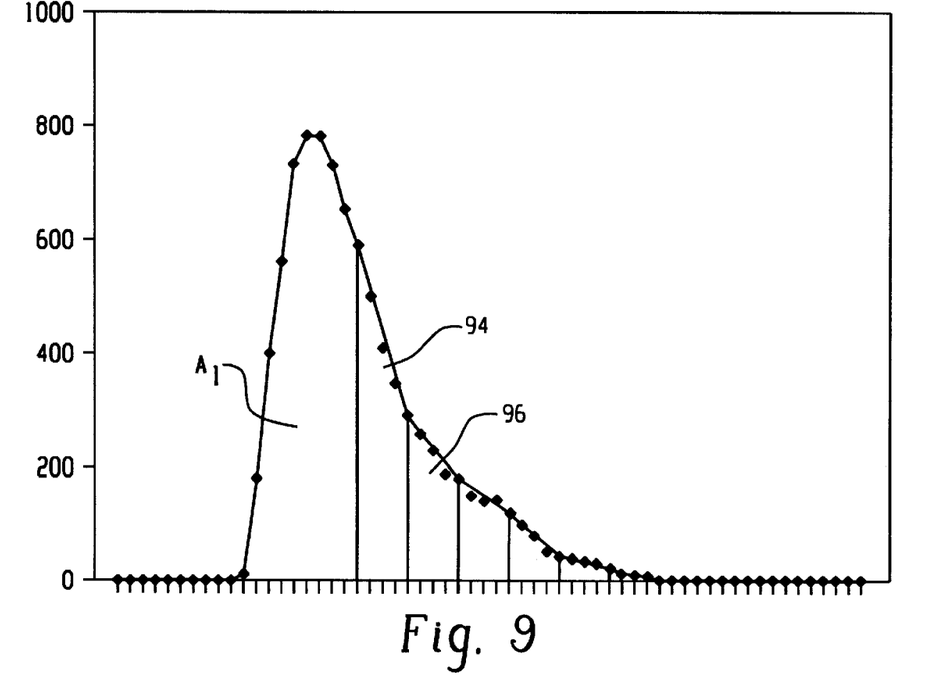

With reference now to the embodiment illustrated in FIG. 8, the processor 26 (FIG. 1) calculates an estimate of the area of the pulse tail $A_2$ by assuming the area to be a defined geometric shape, for instance, triangular, as illustrated. Those skilled in the art will recognize that this embodiment may severely underestimate the total pulse area or energy if pile-up occurs early on as indicated by triangle 90. This error is acceptable for those situations where the pulse rate is sufficiently high to make the storage device 66 (FIG. 1) to retrieve estimator ratios or functions infeasible. Alternatively, this method may be refined by reducing the estimated pulse tail to two or more geometric shapes as indicated by FIG. 9 areas 94 and 96.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A nuclear camera including a plurality of detector heads mounted for movement around a subject in an examination region and a processor for reconstructing signals from the detector heads into an image representation, each detector head comprising:
   a means for converting each received radiation event into a flash of light;
   a means for generating a sampling characteristic of the light flash in response to each received light flash;
   a detecting means for detecting overlapping samplings;
   an integrating means responsive to the detecting means for integrating samples to generate integrated samples, the integrating means integrating an overlapping sampling between an initial point and an overlap point to produce a partial integrated sampling value;
   a means for calculating a ratio of the integrated samples of a calibration event at selected sample times to an integrated sample integrated over the entire calibration event;
   a multiplying means communicating with the integrating means for multiplying the partial integrated sampling value by the calculated ratio to produce a remainder; and
   an adding means communicating with the multiplying means for adding the remainder to the partial integrated sampling value obtain a sampling value.

2. The nuclear camera as set forth in claim 1, wherein the multiplying means includes a plurality of estimated remainders corresponding to integrated sampling values and selected sampling times from a calibration event, the multiplying means selecting an estimated remainder corresponding to the overlap point.

3. A nuclear camera including:
   at least one detector head mounted for movement around a subject in an examination region, each detector head comprising:
      a scintillation crystal that converts each received radiation event into a flash of light,
      an array of photo multiplier tubes arranged to receive the light flashes from the scintillation crystal, each photo multiplier tube generating an analog tube output pulse in response to each received light flash, and
      a plurality of analog-to-digital converters, at least one of the analog-to-digital converters being connected with each photo multiplier tube for converting its analog tube output pulse to a series of digital individual tube output values; and
   a processor that integrates the series of digital values corresponding to a first pulse until the first to occur of the end of the first pulse and the detection of a beginning of an overlapping second pulse, in response to detecting the beginning of the overlapping second pulse, the processor accesses an estimator function to estimate a remainder of the first pulse, the processor including:
      a storage device which stores the estimator function derived from a calibration radiation event, the estimator function including a plurality of ratios of portions of the calibration event at selected sampling times,
      a multiplier for multiplying a ratio corresponding to a sampling characteristic of the first event at the time which the second event is detected and the integrated digital values between detection of the first and the second events to produce an estimated remainder, and,
      an adder for adding the integrated digital values and the estimated remainder.

4. In a medical imaging device for imaging an area of interest by detecting radiation events, a method of estimating truncated events comprising:
   determining at least one estimator function for the medical imaging device by sampling at least one calibration event and calculating ratios of combined digital samples at selected sampling times to a sum of digital samples combined over the entire calibration event;
   detecting a first event of interest;
   detecting interruption of the first event by a second event; and,
   based on the estimator function, estimating a remainder of the first event of interest following detection of interruption by the second event.

5. The method of estimating as set forth in claim 4, further comprising:
   for the first event, digitally sampling the detected event at a sampling rate;
   combining digital samples from the first detected event; and,
   ceasing the combining upon detection of the second event.

6. The method of estimating as set forth in claim 5, further comprising:

for the first event, totaling the combined digital samples of the detected event and the estimated remainder.

7. The method of estimating as set forth in claim 4, wherein the estimating a remainder step includes:
  based on a sampling time substantially coincident with the detection of the interruption, retrieving a calculated ratio; and,
  multiplying the combined digital samples and the retrieved ratio.

8. The method of estimating as set forth in claim 4, wherein the determining an estimator function step further includes:
  associating combined digital samples from the calibration event with the calculated ratios to produce a plurality of remaining area estimates.

9. The method of estimating as set forth in claim 8, wherein the estimating a remainder step includes:
  determining a one of the remaining area estimates corresponding to combined digital samples, and a sample time of detection of the second event.

10. The method of estimating as set forth in claim 4, further including, upon detection of the second event:
  combining samples of the second event; and,
  removing the estimated remainder of the first event from the combined second event samples.

11. A method of estimating an energy of an event detected by a medical imaging device, the method including:
  determining a family of estimator functions for the medical imaging device from calibration events by calculating ratios of combined samples up to selected sampling times within a portion of a calibration event to combined samples over the entire calibration event;
  detecting a first event;
  sampling the detected event at a sampling rate;
  combining the samples from the first detected event;
  detecting a second event partially coincident with the first event;
  ceasing combining the samples in response to detecting the second event; and
  estimating a remainder representing an estimate of combined samples of the first event following detection of the second event.

12. The method of estimating as set forth in claim 11, further including:
  for the first event, totaling the combined samples of the detected first event and the estimated remainder.

13. The method of estimating as set forth in claim 11, further including on detection of the second event:
  combining sampled values to generate a second event combined value; and,
  removing the estimated remainder of the first event from the second event combined values.

14. The method of estimating as set forth in claim 11, wherein the remainder estimating step includes:
  based on a sampling time substantially coincident with the detection of the second event, retrieving a corresponding ratio; and,
  multiplying the combined samples and the retrieved ratio.

15. The method of estimating as set forth in claim 11, wherein the estimator function determining step further includes:

combining combined calibration samples up to selected times with the corresponding ratios to produce a plurality of remaining area estimates.

16. The method of estimating as set forth in claim 15, wherein the remainder estimating step includes:
  based on combined samples of the first event before detection of the second event, and the detection time of the second event, retrieving the remaining area estimate.

17. The method of estimating as set forth in claim 11, wherein the remainder estimating step includes:
  determining an area under at least two points of an estimated pulse tail curve generated from the calibration events.

18. A nuclear camera comprising:
  a radiation receiving face that emits a flash of light responsive to impingement of radiation;
  an array of photodetectors arranged to detect the flash of light and output a series of digital values characteristic of the flash of light;
  a calibration memory which stores measured area ratios that quantitatively characterize pulse remainders at selected times during integration of a calibration pulse; and
  a processor communicating with the array of photodetectors, the processor integrating the output of each selected photodetector until a pulse pile-up is detected to produce a pulse area;
  responsive to the detection of a pulse pile-up on the selected photodetector output, the processor generating the pulse area from the integrated output up to the detected pulse pile-up and the stored area ratio from the calibration memory.

19. A nuclear camera comprising:
  a means for converting radiation into scintillation events;
  an array of individual means for converting each scintillation event into an analog electrical pulse;
  a means for digitizing the analog electrical pulse individually from each of the individual converting means; and
  a means for computing a pulse area of the digitized electrical pulse from each individual converting means individually, the computing means performing the steps of:
    individually integrating the digitized electrical pulse from each individual converting means to generate a pulse area;
    responsive to an intervention of a second digitized electrical pulse from the same individual converting means during the integrating of the digitized electrical pulse, terminating the integrating of the digitized electrical pulse, estimating a remainder area of the digitized electrical pulse using an area ratio of integrated areas of portions or all of a pre-recorded calibration pulse, and summing the integrated area and the remainder area to produce the pulse area.

20. The nuclear camera as set forth in claim 19, wherein the area ratio is selected based on a time during the integrating of the digitized electrical pulse at which the second digitized electrical pulse intervenes.

\* \* \* \* \*